United States Patent [19]

Pischel

[11] Patent Number: 5,543,309
[45] Date of Patent: Aug. 6, 1996

[54] CARRIER CONTAINING ENZYMES FOR TREATING SEWAGE SLUDGE

[76] Inventor: Ernie Pischel, P.O. Box 174, Belfair, Wash. 98528

[21] Appl. No.: 345,847

[22] Filed: Nov. 28, 1994

[51] Int. Cl.$^6$ .......................... C12N 11/02; C12N 11/12; C12M 1/40; B09B 3/00
[52] U.S. Cl. .................. 435/177; 435/179; 435/182; 435/262.5; 435/283.1
[58] Field of Search ..................... 435/174, 177, 435/178, 179, 182, 262.5, 288

[56] References Cited

U.S. PATENT DOCUMENTS

| | | | |
|---|---|---|---|
| 3,242,055 | 3/1966 | De Lucia | 435/177 X |
| 3,767,790 | 10/1973 | Guttag | 435/182 X |
| 4,006,059 | 2/1977 | Butler | 195/68 |
| 5,275,943 | 1/1994 | Di Turo | 435/179 |
| 5,284,587 | 2/1994 | Wong et al. | 435/182 X |

*Primary Examiner*—David M. Naff
*Attorney, Agent, or Firm*—Thomas W. Secrest

[57] ABSTRACT

A carrier is prepared containing bacteria and/or enzymes for degrading sewage sludge. The carrier can be in the form of a gel containing coloring matter and optionally a deodorant, or in the form of a core for a roll of toilet tissue or a roll of towels. In a preferred embodiment, the carrier is in the form of a tube that is used as a core for a roll of toilet tissue. The tube is formed from at least two layers made from cellulose bonded together with a water soluble bonding agent. Enzymes and/or bacteria can be in a slurry of cellulose pulp used to make the core, in the bonding agent, or in a coating or strip on an inside and/or outside layer. The tube contains a plurality of sets of circumferential perforations that enable, after removing toilet tissue, readily breaking the tube into a plurality of small pieces that can be flushed down a toilet bowl into a sewage system where the pieces disintegrate and release the enzymes and/or bacteria. The tube may also contain a plurality of holes that allow an aqueous medium to readily seep between the layers to assist in disintegration.

2 Claims, 4 Drawing Sheets

CARRIER CONTAINING ENZYMES FOR TREATING SEWAGE SLUDGE

CROSS-REFERENCES TO RELATED APPLICATIONS

There is no related application.

STATEMENT AS TO RIGHTS TO INVENTIONS MADE UNDER FEDERALLY SPONSORED RESEARCH AND DEVELOPMENT

This invention was made independently of federal funds.

BACKGROUND OF THE INVENTION

1. Field of the Invention

The field invention of the invention is related to sanitation and disposal of sewage. The sewage can originate in the household, in office buildings and manufacturing facilities as well as recreational facilities, to name a few of the places of origin. Many households have a septic system and are not connected to an urban sewage treatment plant. After a period of time, sludge accumulates in the septic tank. It is necessary to call a septic cleaning system to remove the sludge from the septic tank. The sludge can be spread on the ground and can be worked into the ground over a period of time. Or, the sludge can be incinerated.

This invention is directed to the lessening of the accumulation of sludge. It is possible to use the subject matter of this invention to lessen the accumulation of sludge and thereby lessen the number of times it is necessary to remove sludge from the septic tank. Further, this invention is beneficial to sewage treatment systems in addition to septic systems. A septic system is usually used in an isolated situation such as by a person residing in a low-density population area. A sewage treatment system is used in a high-density population area and treats the sewage so as to render it innocuous. With this invention, the accumulation of sewage sludge is lessened and, therefore, it is not necessary to spread sewage sludge as often as before this invention was made or to incinerate as much sewage sludge as before this invention was made.

With this invention there is an inherent control on the introduction of enzymes into a septic tank or sewage treatment facility. The number of cores of bathroom tissue and the quantity of enzymes is proportional to the number of people using the sewage facilities. With more people there is more sewage and there is used more bathroom tissue and there is available more cores of bathroom tissue resulting in more enzymes introduced into the sewage sludge. The converse is also true.

It is the understanding of the inventors that a large part of the sewage sludge is other than human waste such as food wastes like fat and meat and vegetables; soap and detergents and cleaning agents; paper and cellulose products; and, the like. Human wastes can be efficiently treated by sewage treatment factors. The above enumerated items, other than human waste, are not readily treated by sewage treatment facilities. Therefore, enzymes are added to decompose these components of sewage. An easy and efficient and inexpensive way to add enzymes to sewage sludge is by dissolving a core of bathroom tissue or a deodorant and/or coloring agent containing enzymes in the sewage sludge.

It is the understanding of the inventor that truckloads of sewage are transported each day from the sewage treatment plant in the city of Seattle, Wash. to the farmland of eastern Washington and spread on the farmland to get rid of the sludge. With this invention, it may be possible to lessen the number of truckloads of sewage sludge transported from an urban area to a less populated farm area.

2. Description of the Prior Art

A patent search was made at the Engineering Library at the University of Washington in Seattle, Wash. and no prior art was found directed to the same subject matter as the subject matter of this invention. This invention teaches the adding of bacteria and enzymes to sewage sludge in a unique manner so as to reduce the quantity of sewage sludge. Sewage sludge comprises solidified mixtures of human waste, fat, protein, starch and paper. With the addition of certain enzymes, the amount of human waste, fat, protein, starch and paper is transformed into liquids and gases and, therefore, the quantity of sewage sludge is lessened.

SUMMARY

This invention is directed to a carrier for incorporating bacteria and enzymes for reduction of the solids in sewage. The carrier should be low-cost, readily available, readily and easily usable by almost all people and easy to manufacture. Such a carrier for enzymes can be a core of a roll of bathroom tissue for toilet paper.

The tubular core can be broken into smaller units and flushed in the bowl of a toilet. A toilet comprises a water reservoir operatively connecting with a bowl which can be flushed.

The bacteria and enzymes can be introduced into the core in many ways. One way of introducing the bacteria and enzymes is in the pulp slurry for making the core. The core can be made from a slurry of cellulose pulp. The bacteria and enzymes can be in this slurry. Further, there is an adhesive used in making the core and in the adhesive there can be bacteria and enzymes for sewage sludge. Another way is to attach a packet of bacteria and enzymes to the core. The core on contacting water will release the bacteria and enzymes. Still, a further way is to coat the core such as by spraying, sprinkling, brushing or other suitable means with bacteria and enzymes so that the core is carrying bacteria and enzymes to the sewage sludge. The coating comprising enzymes and bacteria may be applied on the inside or on the outside of the core.

There are many objects and advantages of this invention, one of which is an inexpensive way to lessen solids in sewage sludge.

Another object is an easy way to lessen the amount of sewage sludge.

Another feature is that the invention can be distributed as a consumer-oriented product.

Another object is that the invention can be readily introduced into the manufacturing process of certain household objects and which household objects can be discarded into the sewage processing system.

An additional object is the assistance in cleaning waste water and keeping ground water, streams and rivers clean.

A further object is that the invention does not dilute the cellulose fibers on naturally occurring products such as in wood, agricultural stalks and plants such as in straw and the like.

Another beneficial object is to reduce pollution and to improve the environment.

Another important object is to assist in the purification of sewage sludge.

An additional object is a new technique for lessening the disposal of sewage with the use of readily available and inexpensive materials.

Another important object is to maintain in a clean condition or return to a clean condition drain pipes in the drain field in the sewage disposal plants such a septic tank as the bacteria and the enzymes react with the sludge in the drain pipes.

An additional object is a provision of a means and a method for reducing the number of times a septic tank must be cleaned or sewage treatment facility must be cleaned.

A further important object is with this invention there is less sewage to transport and to spread and/or to incinerate in order to dispose of solids.

Another important object is to have a correlation between the number of people using sewage facilities and the quantity of enzymes introduced into the sewage facilities as evidenced by the number of rolls of bathroom tissue and the corresponding number of cores of bathroom tissue.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

In the drawings it is seen that

FIG. 1 is an elevational view of a core for toilet tissue or paper towels and the like;

DESCRIPTION OF THE PREFERRED EMBODIMENT

Figure 1:
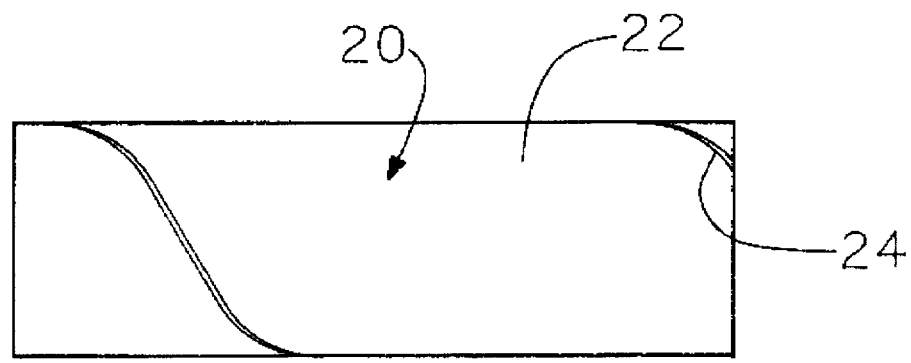

In FIG. 1 it is seen that there is a core for toilet tissue. There is a core 20 comprising an outer layer 22 and an inner layer 24 for strength and rigidity and for a long length.

The core 20 is, generally, of a cellulose base material.

The source of the cellulose is generally a tree, although there can be other sources such as straw and other agricultural products comprising cellulose in fiber form.

Cellulose is a naturally-occurring substance as a building block in trees and stalks such as in straw and other agricultural products. Also, cellulose is environmentally friendly as in time it will react to form materials such as water and carbon dioxide and other chemicals.

Figure 2:
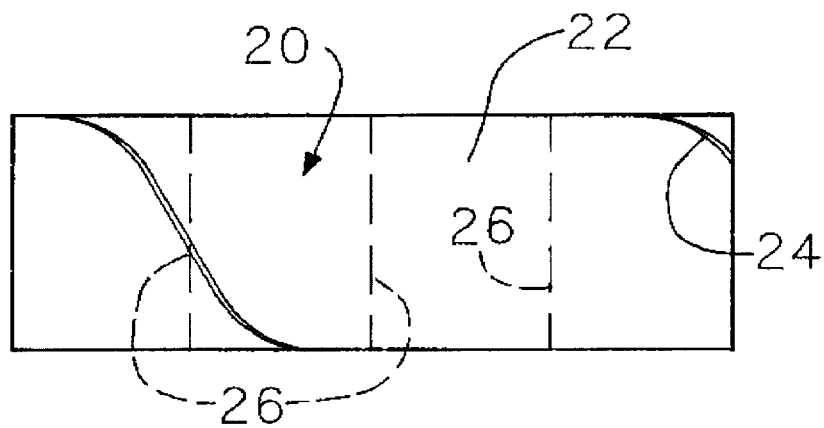
FIG. 2 is an elevational view of the core and illustrates, in phantom lines, perforations for separating the core into smaller units.
Figure 3:
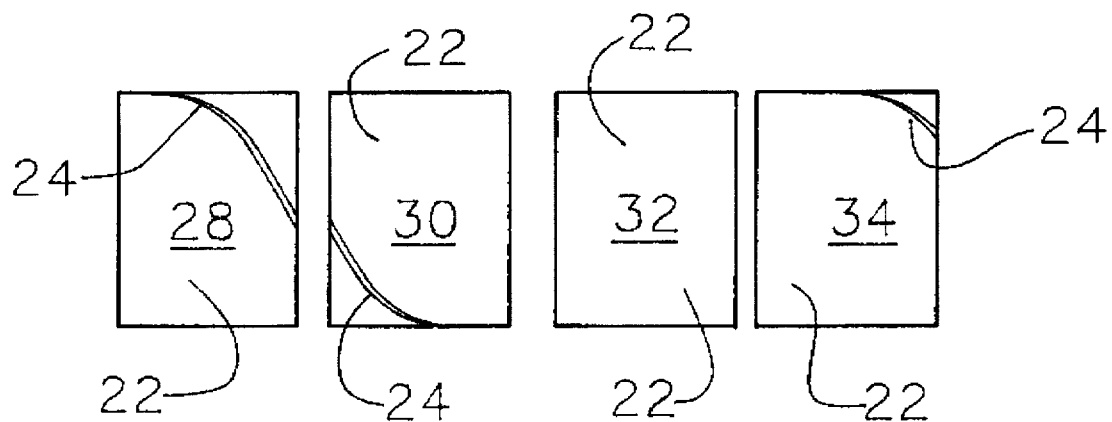
FIG. 3 is an elevational view illustrating the core after it has been separated along the phantom lines of FIG. 2 into four separate smaller units.

In FIG. 2 there is illustrated the core 20 having the outer layer 22 and the inner layer 24. Also, there are three sets of perforations 26. The perforations are for ease of breaking the core into four smaller pieces, see FIG. 3. These four smaller pieces can be identified as 28, 30, 32 and 34.

After a person has removed the toilet tissue from the core 20, it is possible for a person to take the core 20 and readily break the core along the perforations 26 so as to separate the core into smaller units 28, 30, 32 and 34 for ease of disposal in the toilet bowl of a toilet. These small pieces of the core can be thrown into the toilet bowl and be flushed down the toilet and into the septic tank or sewage systems so as to disintegrate into bundles of cellulose fiber.

Figure 4:
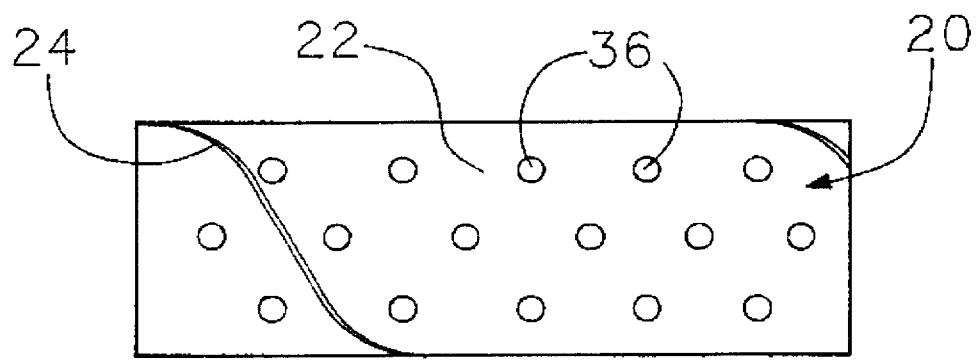
FIG. 4 is an elevational view of a core and illustrates a number of holes in the core for ease of disintegration of the core in the sewage sludge.

In FIG. 4 there is illustrated another form for the core 20 comprising outer layer 22 and the inner layer 24. This form or species has holes 36. These holes allow the water to readily seep between the layers 22 and 24 to assist in the disintegration of the core 20 in the sewage sludge or in water.

Figure 5:
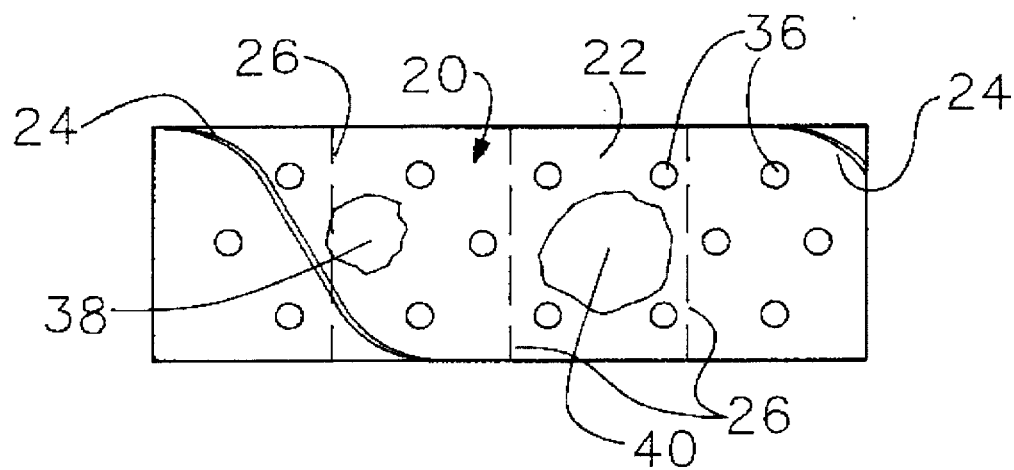
FIG. 5 is an elevational view of the core and, illustrates by phantom lines, perforations in the core for breaking the core into smaller units, holes in the core for more rapid disintegration and dissolving of the core in sewage sludge; and at the left a breaking away of the outer layer of the core so that the adhesive between the two layers of the core is exposed and which adhesive can be a carrier for enzymes; and, the broken part in the right of the core illustrates the two layers of the core being broken away so as to show a coating inside of the core and which coating contains for producing enzymes for breaking down the sludge.

In FIG. 5 there is illustrated a core 20 out of the outer layer 22 of cellulose and the inner layer 24 of cellulose. There are three spaced apart perforations 26 for ease of breaking the core into smaller units.

It is seen that part of the outer layer 22 has been removed so as to expose a glue interface between the outer layer 22 and the inner layer 24. This glue interface can carry bacteria and enzymes for working on solids in sewage sludge. The solids can be human waste, fats and grease, starch and protein among other items.

Also, in FIG. 5 it is that the layer 22 and the inner layer 24 have been removed so as to have a window showing the coating 40 on the inside of the tube or in the inside of the inner layer 24 around the inner surface of the liner 24. The coating can contain bacteria and enzymes for reacting with the solids in sewage sludge.

The core 20, as illustrated in FIGS. 1, 2, 3, 4 and 5, can comprise a glue or adhesive 38 between the outer 22 and the inner layer 24. This glue can be a glue which dissolves in water or is readily soluble in water. The glue can also be a carrier for bacteria and enzymes for reacting with sludge within sewage sludge.

Figure 6:
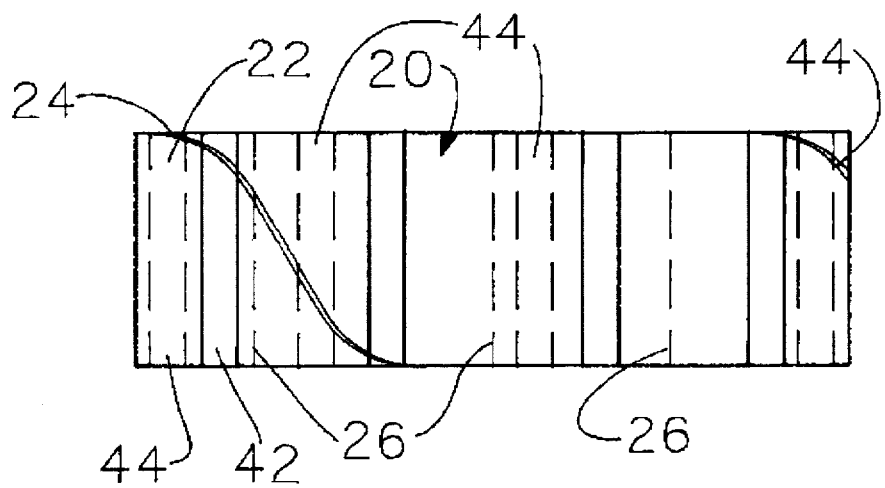
FIG. 6 is an elevational view of the core and by solid circumferential lines on the outside of the core illustrates a carrier for enzymes for reducing the sludge in sewage sludge and by phantom circumferential lines on the inside of the core illustrates a carrier for enzymes for reducing the sludge in sewage sludge.

In FIG. 6 there is illustrated a core 20 having an outer layer 22 and an inner layer 24.

On the outside of the outer layer 22 there is a strip 42. On the inside of the inner layer 24 there is a strip 44. The strips 42 and 44 are carriers for bacteria and enzymes for reacting with solids in sewage sludge. The strips 42 and 44 readily disintegrate upon contacting water and liquids in the sewage sludge.

Figure 7:
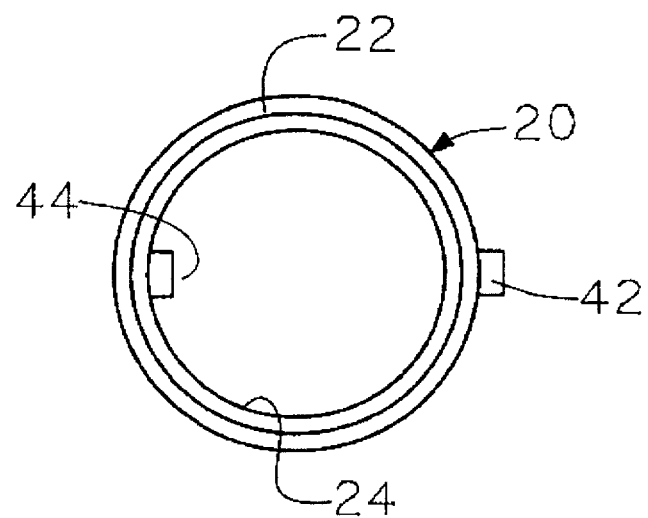
FIG. 7 is an end elevational view of the core and illustrates the two layers of the core and on the inside of the core there is illustrated a phantom block which contains enzymes for reducing the sludge in the sewage sludge; and, on the outside of the core there is illustrated a phantom block which contains bacteria for reducing the sludge in sewage sludge.

FIG. 7 is an end view of FIG. 6 and illustrates the outer strip 42 and the inner strip 44.

Figure 8:
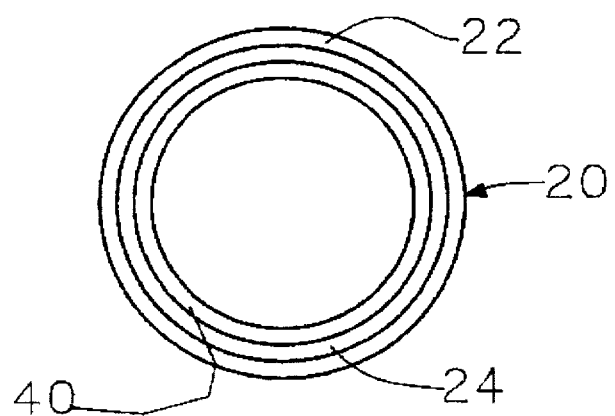
FIG. 8 is an end elevational view showing the core for a roll of bathroom tissue and which core comprises an inner layer, an outer layer and an outer coating for bacteria and enzymes.

In FIG. 8, an end view, there is illustrated the core 20 having an outer liner 22 and an inner 24. On the inside of the inner liner 24, there is a coating 40. In this regard see FIG. 5. The coating 40 is a carrier for bacteria and enzymes for reacting with the solids in sewage sludge.

Figure 9:
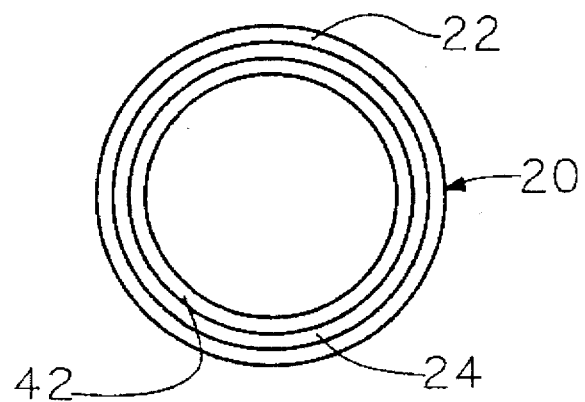
FIG. 9 is an end elevational view of a core for bathroom tissue and which core comprises an inner layer and an outer layer and an inner coating inside of the inner layer and which inner coating comprises bacteria and enzymes.

In FIG. 9, an end view, there is illustrated the core 20 having an outer liner 22 and an inner liner 24. On the inside of the inner liner 24, there is a coating 42. In this regard, see FIG. 5. The coating 42 is a carrier for bacteria and enzymes for reacting with the solids in sewage sludge.

Figure 10:
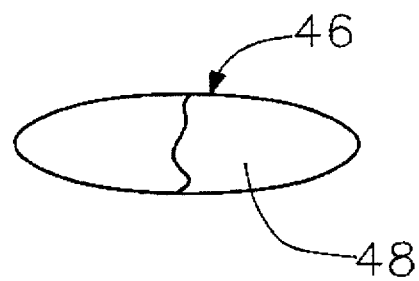
FIG. 10 is an end elevational view of a solid disk with part of the disk broken away to show a cross section of a mixture of coloring material, bacteria and enzymes and can include a deodorant; and, FIG. 11 is a side elevational view of a container showing part of the container broken away to reveal a gel and/or a liquid containing coloring matter and enzymes and bacteria and which also may contain a deodorant as well as a cap having passageways for the gel and/or liquid to seep out of the container.

FIG. 10 is side elevational view of a solid disk 46 with part of the disk broken away to show a mixture 48. The mixture 48 comprises coloring matter and bacteria and enzymes. Also, the mixture 48 may comprise a deodorant. The solid disk 46 can be placed in the water reservoir of a toilet. In time, the solid disk 46 dissolves. In this manner there is introduced into water in the water reservoir a coloring agent, usually blue, bacteria and enzymes for reacting with the sludge in sewage sludge. There also may be introduced a deodorant.

Figure 11:
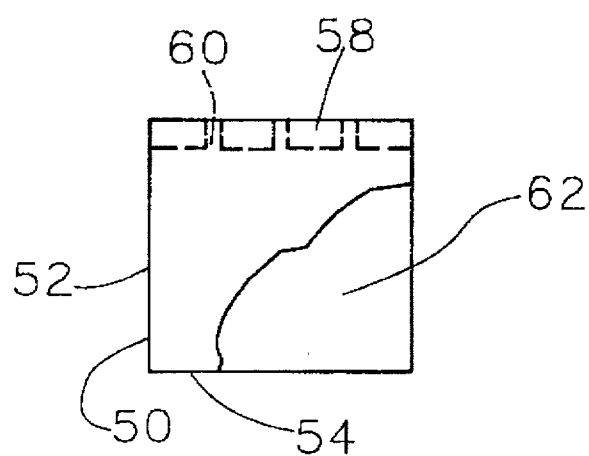

FIG. 11 is a side elevational view of a container 50 having a side 52 and a bottom 54. The side 52 may be in the form of a cylinder. There is an open end at the opposite end of the side 52 with respect to the bottom 54. There is a cap 58 for fitting into and over the open end. In the cap 58 there is a series of passageways. In the container 50 there is a gel and/or liquid 52 containing coloring matter and bacteria and enzymes. The gel and/or liquid 62 may also contain deodorant. The container 50 is placed in the water closet of the toilet. In time, the gel and/or liquid 62 dissolves and disperses in the water in the water reservoir to release bacteria and enzymes for reacting with the sludge in sewage sludge. The water can seep into the container 52 through passageways 60 and dissolve some of the gel and/or liquid 62 and then seep out of the container 50 through the passageways 60. Generally, the coloring matter in the gel and/or liquid 62 will be blue. The gel and/or liquid 62 can also contain a deodorant in addition to the coloring matter and the bacteria and enzymes.

There may be used a blend of scientifically enhanced enzymes that act as a catalytic agent for speeding up the degradation rate of organic waste.

The method is the natural digestion of their natural food by living friendly bacteria. Their food is organic waste matter. The bacteria recycle wastes back to the simple basic parts of soil, air, and water from which they were formed from. Used by the natural laws that govern them, the bacteria feed on wastes by digesting, liquifying and recycling the wastes to actually enrich the environment. The enzymes produce NO POISONS or damaging side effects in the process. Their action is complete.

Today, many of the septic systems don't receive an adequate bacteria supply from natural sources. The use of acids, caustics, detergents (and modern bacteriostats and disinfectants to kill germs), also kill the friendly bacteria the systems must have to operate trouble-free, healthfully, and without great maintenance costs.

One composition may be composed of: 8 scientifically enhanced biostrains 3 strains of *Bacillus subtilis*

1 strain of *Bacillus licheniformis*

1 strain of *Pseudomonas aeruginosa*

1 strain of *Pseudomonas stutzeri*

1 strain of *Escherichia hermanii*

1 strain of *Pseudomonas flourescens*.

These bacteria strains work together with the septic system's naturally occurring bacteria to aid in a quicker breakdown of difficult compounds and to improve the overall performance of any septic system. The enzymes help to liquify and digest the solid wastes. Some of these enzymes are:

Lipase enzymes—These enzymes attack all fats and greases, break down their molecular structure and dissolve them.

Amylase enzymes—These enzymes break down all starches they contact, and as with Lipase enzymes the molecular structure is broken down and the starches are dissolved.

Proease—This type of enzyme literally feeds on, breaks down and dissolves all organic wastes of the protein family. The protein family waste is the most common waste found in septic systems.

All the mentioned bacteria are Salmonella negative, non-pathogenic, non-toxic and harmless to animals or man.

It is desirable that the bacteria count be at least 1 billion organisms per ounce.

The chief components of the feces are water, undigested food residues, bile pigments, enzymes, leukocytes, bacteria, and products of the secretory activity of the intestine, e.g., mucus and desquamated epithelial cells. The normal brownish color of the feces is due chiefly to stercobilin, a product formed by bacterial degradation of one of the normal bile pigments, bilirubin. The odor of feces is due principally to indole and skatole, formed by the deamination and decarboxylation of tryptophan, and to hydrogen sulfide, produced form cystine by bacterial action in the large intestine.

From the foregoing, it is seen that has been provided a teaching for reducing the volume of sewage sludge by an easy and inexpensive introduction of enzymes and bacteria into the sewage sludge. the introduction of the enzymes and the bacteria can be accomplished by almost every person.

What I claim is:

1. A cylindrical core for a roll of toilet tissue containing one or more enzymes for commingling with components of sewage in an aqueous medium to degrade sewage comprising:

a. said core being in the form of a tube prepared from at least two cylindrical layers made from cellulose and bonded together with water soluble bonding agent;

b. one of said layers being an outside layer and another of said layers being an inside layer;

c. said one or more enzymes being contained by at least one of said bonding agent, a coating on at least one of said layers or a strip on at least one of said layers; and d. said tube containing a plurality of sets of circumferential perforations that enable, after removing toilet tissue from said core, readily breaking said core into a plurality of small pieces that can be flushed down the bowl of a toilet into a sewage system where the pieces disintegrate and release said one or more enzymes to degrade sewage.

2. A process for making a cylindrical core for a roll of toilet tissue containing one or more enzymes for commingling with components of sewage in an aqueous medium to degrade sewage comprising:

a. forming said core as a tube containing at least two cylindrical layers made from cellulose and bonded together with a water soluble bonding agent such that one of said layers is an outside layer and another of said layers is an inside layer;

b. applying said one or more enzymes to said tube by at least one of adding said one or more enzymes to said bonding agent, applying a coating containing said one or more enzymes to at least one of said layers or forming a strip containing said one or more enzymes on at least one of said layers; and c. forming a plurality of sets of circumferential perforations in said tube that enable, after removing toilet tissue from said core, readily breaking said core into a plurality of small pieces that can be flushed down a toilet bowl into a sewage system where the pieces disintegrate and release said one or more enzymes to degrade sewage.

* * * * *